United States Patent [19]
KenKnight et al.

[11] Patent Number: 5,314,464
[45] Date of Patent: May 24, 1994

[54] METHOD AND APPLICATOR TOOL FOR IMPLANTING CARDIAC DEFIBRILLATION ELECTRODES

[75] Inventors: Bruce H. KenKnight, Minneapolis; Jeffrey A. Hall, Bloomington; William J. Eastman, Maple Grove, all of Minn.

[73] Assignee: Cardiac Pacemakers, Inc., St. Paul, Minn.

[21] Appl. No.: 954,514

[22] Filed: Sep. 30, 1992

[51] Int. Cl.⁵ ............................................. A61N 1/05
[52] U.S. Cl. .................................. 607/132; 607/130; 607/116
[58] Field of Search ............. 128/783, 784, 785, 786, 128/642, 419 P, 419 D; 607/115, 116, 119, 122, 129–130, 132, 9

[56] References Cited
U.S. PATENT DOCUMENTS

| | | |
|---|---|---|
| 4,271,846 | 6/1981 | Little ................................. 128/785 |
| 4,345,606 | 8/1982 | Littleford ........................... 128/784 |
| 4,886,065 | 12/1989 | Collins, Jr. ..................... 128/785 X |
| 5,036,854 | 8/1991 | Schollmeyer et al. ......... 128/785 X |

*Primary Examiner*—William E. Kamm
*Assistant Examiner*—Jeffrey R. Jastrzab
*Attorney, Agent, or Firm*—Keck, Mahin & Cate

[57] ABSTRACT

A tool and method for inserting cardiac defibrillation electrodes into a patient. The tool includes an elongated electrode support tube having a rounded distal end and a proximal end; a finger grip circumferentially connected about the electrode support tube toward the proximal end thereof; and an actuating rod slidably disposed coextensively within the electrode support tube and extending beyond the rounded distal end and the proximal end of the electrode support tube. A blunt conically shaped distal tip is connected to the distal end of the actuating rod, the distal tip having a base with a diameter larger than the diameter of the electrode support tube, and an inner surface for engaging the rounded distal end of the electrode support tube. A palm member is connected to the proximal end of the actuating rod to facilitate hand manipulation of the tool. In addition, a resilient device (preferably, a spring) is included for exerting a force on the actuating rod tending to withdraw the actuating rod out through the proximal end of the electrode support tube, such withdrawal being prevented by the engagement of the inner surface of the distal tip with the rounded distal end of the electrode support tube. In use, a cardiac defibrillation electrode is wrapped around the electrode support tube with the distal end of the electrode immobilized between the distal tip of the tool and the rounded distal end of the electrode support tube.

12 Claims, 2 Drawing Sheets

METHOD AND APPLICATOR TOOL FOR IMPLANTING CARDIAC DEFIBRILLATION ELECTRODES

This application is related to U.S. patent application Ser. No. 07/954,616 filed concurrently herewith and entitled: Defibrillation Patch Electrode Having Conductor-Free Resilient Zone For Minimally Invasive Deployment.

BACKGROUND OF THE INVENTION

The present invention relates to a minimally invasive method and applicator tool for implanting cardiac cardioversion/defibrillation electrodes, especially wire patch electrodes and cardiac electrodes similar to those set out in the aforementioned concurrently filed application.

Epicardial cardioversion/defibrillation electrodes most often require major thoracic surgery (median sternotomy or thoracotomy) for implantation. This highly invasive surgical procedure leads to substantial patient morbidity. By eliminating the need for these invasive surgical procedures, implantable defibrillation therapy acceptance for certain patient populations may increase.

For electrode configurations not employing endocardial electrode(s), two separate epicardial electrodes of opposite polarity (normally located on the left and right ventricles) are required for efficacious defibrillation therapy. Recently, much emphasis has been placed on reducing post-operative patient morbidity by limiting the invasiveness of requisite surgical procedures for application of internal defibrillation therapy. The present invention addresses these problems by allowing intrathoracic implantation of conventional wire mesh patch electrodes through small (1-2 cm) chest wall defects (normally intercostal).

Prior attempts to utilize a special tool for patch electrode introduction are exemplified in U.S. Pat. No. 4,291,707—Heilman and U.S. Pat. No. 4,270,549—Heilman et al. Specifically, reference is made to FIG. 4 in the '707 patent and FIGS. 4 and 7 in the '549 patent. Although generally effective, these prior attempts were complicated by (1) maintenance of a substantially planar patch orientation which requires a long cutaneous incision (more invasive) for introduction, (2) lack of remotely actuatable disengagement mechanism, (3) potential tissue trauma during tool extraction.

Probably the most significant disadvantage to these prior attempts is that the electrodes could not be atraumatically introduced through a small circular chest wall defect. Consequently, either large cutaneous incisions were required or the patches were severely and irreparably deformed during introduction.

SUMMARY OF THE INVENTION

It is a primary object of the present invention to overcome the disadvantages of the prior methods by providing a minimally invasive method and tool for implanting cardiac defibrillation electrodes, especially wire patch electrodes and cardiac electrodes similar to that set out in the aforementioned concurrently filed application.

A further object of the present invention is to provide a minimally invasive method and tool for implanting cardiac wire patch defibrillation electrodes, without severely or irreparably deforming the electrodes.

To achieve this and other objects, the present invention provides an applicator tool and method for introducing a patch electrode within the thorax for treatment of life-threatening tachyarrhythmias. (The term "patch electrode" is hereinafter understood to encompass conventional cardiac wire patch electrodes, as well as the electrodes set out in the concurrently filed application.) The applicator tool assists the surgeon by providing a rigid substructure onto which the patch electrode is temporarily affixed during passage through chest wall tissues. By supporting the flexible patch electrode during translation through a restrictive surgical wound, unfavorable electrode deformation is avoided and proper electrode positioning is facilitated.

The applicator tool of the present invention comprises a generally tubular structure which engages the patch electrode at a distal end and thereby securely immobilizes the electrode during introduction. Once positioned in a desirable location, the patch electrode is deployed by disengaging the electrode from the tool. The tool is then withdrawn and the electrode affixed on or near the heart surface using techniques known to those familiar with the art, such as staples or sutures.

DETAILED DESCRIPTION OF THE PREFERRED EMBODIMENT

Figure 1:
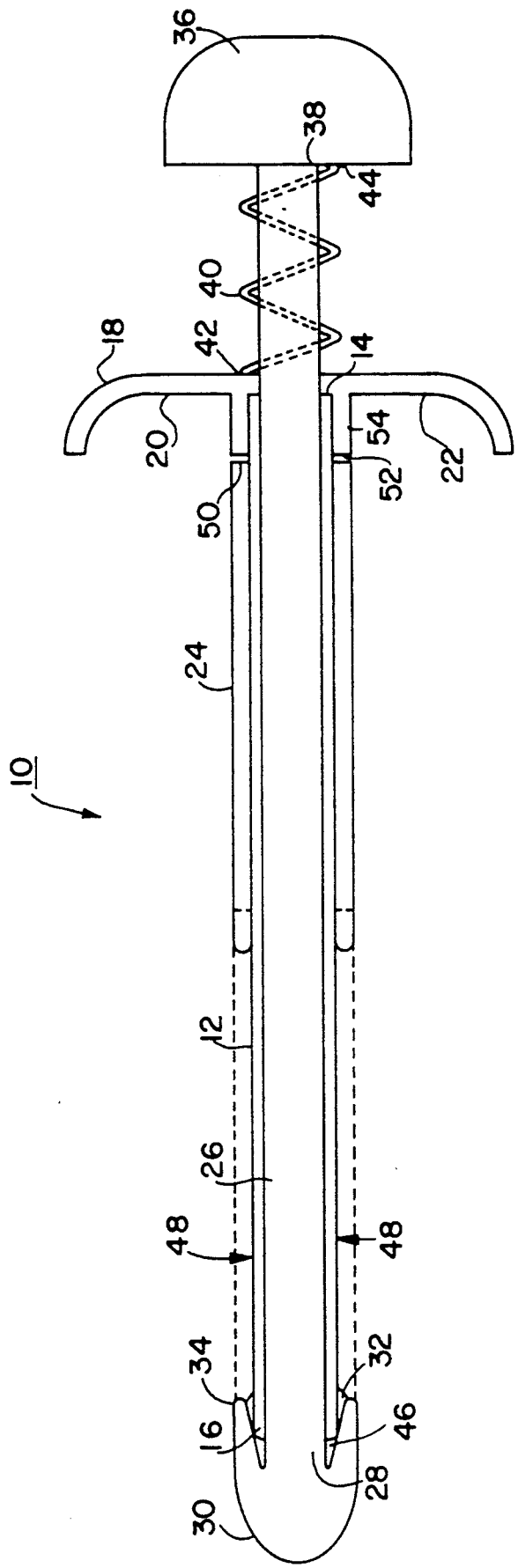
FIG. 1 illustrates an applicator tool according to a preferred embodiment of the present invention.

With reference to FIG. 1, a preferred embodiment of the applicator tool will now be described.

According to the preferred embodiment, the applicator tool 10 comprises an outer electrode support tube 12 beginning a a proximal end 14 and terminating at a rounded distal end 16. Also included is a finger grip 18 including a central body portion 19 and two finger hooks 20 and 22, and a slidable sleeve 24 circumferentially surrounding the support tube 12. An actuation rod 26 extends through the finger grip 18 and internally through the length of the support tube 12, exiting at both the distal end 16 and the proximal end 14 of the support tube 12. Securely connected to a distal end 28 of the actuating rod 26, is a conically shaped distal tip 30 having an inner surface 32 and a beveled edge 34. The distal tip 30 is connected to the actuating rod 26 by thread or other conventional connecting means (not shown). A portion of the distal tip 30 has a diameter larger than the diameter of the electrode support tube 12, such that a portion of the inner surface 32 also has a diameter larger than the diameter of the electrode support tube 12. A palm member 36 is connected to a proximal end 38 of the actuating rod 26, while a compressed coil spring 40 circumferentially surrounds the actuation rod 26 between the palm member 36 and the finger grip 18. In addition, one end of the spring 40 bears against a surface 42 on the finger grip 18, while the other end of the spring 40 bears against another surface 44 on the palm member 36.

Because the spring 40 is in a compressed state between the surfaces 42 and 44, a force is exerted on the actuating rod 26 which tends to withdraw the actuating rod in a proximal direction (to the right in FIG. 1) from the support tube 12. Consequently, the inner surface 32 of the distal tip 30 is forced to bear against the rounded distal end 16 of the support tube 12.

When the tool 10 is grasped by the hand of the user in a manner allowing further compression of the spring (such as positioning the first two digits of either hand on finger hooks 20 and 22, respectively, while resting the palm member 36 in the palm), distal translation of actuating rod 26 can be achieved by squeezing the finger hooks 20 and 22 in toward the palm member 36. This, in turn, results in physical separation of the rounded distal end 16 from the inner surface 32 of the distal tip 30.

Figure 2:
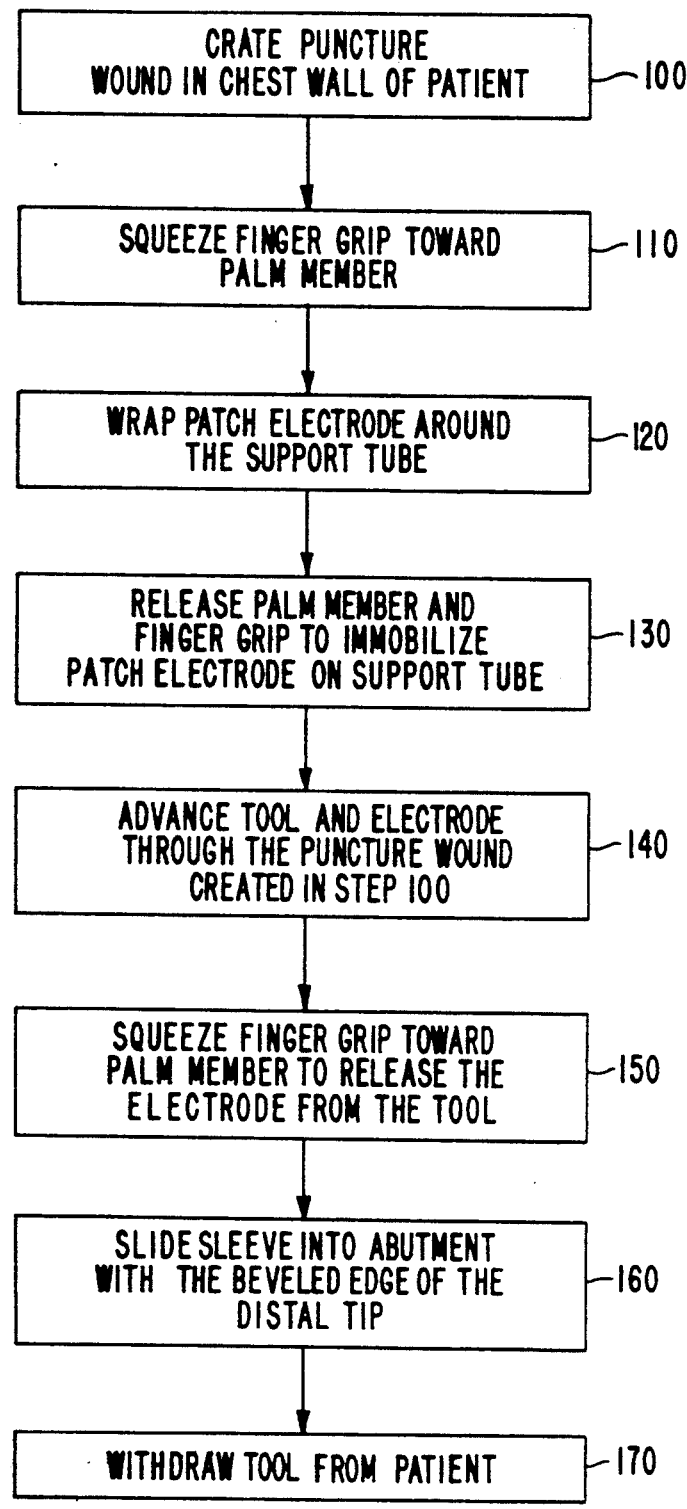
FIG. 2 is a flow chart describing a method for implanting patch electrodes using the applicator tool of FIG. 1.

With reference to FIG. 2, a method for implanting patch electrodes using the applicator tool 10 of FIG. 1 will now be described.

In step 100, a puncture wound is created in the chest wall of a patient receiving the patch electrodes. Preferably, the puncture wound is created in an intercostal region of the chest.

Next, in step 110, the finger grip 18 is squeezed toward the palm member 36, as described above, such that the coil spring 40 is compressed and the distal end 16 separates from the inner surface 32. An annular void 46 is thus revealed between the distal tip 30 and the support tube 12.

During step 120, a patch electrode is wrapped circumferentially around the support tube 12 such that the distal edge of the electrode (not shown) enters the annular void 46 between the distal tip 30 and the support tube 12. A mechanical interference is thus established between distal end 16 and the inner surface 32 by the distal edge of the patch electrode.

According to step 130, by subsequently releasing the palm member 36 and finger grip 18, the spring 40 causes the actuating rod 26 to move longitudinally through the support tube 12 in the proximal direction. The patch electrode is consequently immobilized on the tool 10 by engagement with the distal tip 30 and the support tube 12 between the rounded distal end 16 and the inner surface 32.

In step 140, with the electrode securely but temporarily affixed to the tool 10, the distal tip 30 of the tool 10 is inserted into the puncture wound created in step 100, and the tool 10 and electrode are advanced longitudinally through the puncture wound and into the chest cavity.

Once within the chest cavity in a desired position, according to step 150, the electrode is released from the tool by again manually compressing the spring 40 between the palm member 36 and finger grip 18.

In step 160, the sleeve 24, the proximal end 50 of which was abutting end 52 of cylindrical projection 54 on finger grip 18, is then advanced toward the distal tip 30 and into abutment with the beveled edge 34 formed on the distal tip 30. Phantom lines in FIG. 1 indicate the distal position of the sleeve 24. By sliding the sleeve 24 into contact with the bevelled edge 34, the snagging of tissue is avoided during tool withdrawal.

Once the sleeve 24 is in its distal position, according to step 170, the tool is withdrawn from the patient, leaving the patch electrode in a desired location. The patch electrode can then be sutured or stapled in place using conventional techniques.

The primary advantages of the applicator tool 10 and associated method are many-fold. (1) By sizing the major diameter 48 of the applicator tool 10 such that the circumference of the support tube 12 is equal to or slightly greater than width of the patch electrode, the electrode is protected from unfavorable bending forces which would otherwise be produced during insertion through the chest wall. (2) The recessed structure of the distal tip 30 shields the distal edge of the electrode thereby allowing for uncomplicated passage through the tissue tract. (3) The proximal location of the spring-loaded actuation mechanism allows for simple electrode engagement and disengagement. (4) The beveled edge 34 of the distal tip prevents inadvertent snagging of tissues during tool withdrawal. (5) The blunted shape of the distal tip 30 provides a means for minimally traumatic passage of the tool through the tissues.

In addition to the preferred embodiment herein described, there are several alternative embodiments that may offer the same or other advantages. First, the cross section of the tool need not be circular. An elliptical shape would provide a slightly lower the profile, thereby reducing the amount of tissue spreading in one direction which is important when larger patch electrodes are being introduced between the ribs.

Another alternative involves the addition of means to enhance the reliability of electrode engagement. Examples of such means might include small rigid protrusions that "bite" into the electrode in preferred locations to enhance electrode retention force.

Other actuation means could be employed to create the desired linear translation of the support tube with respect to the electrode engaging distal tip 30. A threaded rod and nut could be used to replace the spring mechanism. Similarly, any means of actively engaging and securely yet temporarily restraining the patch electrode at the distal end of the tool could be accomplished by implementation of multi-bar linkages.

A still further alternative embodiment involves either malleable or pre-curved forms that more effectively conform to the heart to allow better placement of the electrodes within the thorax.

The above description is intended by way of example only and is not intended to limit the present invention in any way except as set forth in the accompanying claims.

We claim:

1. A tool for inserting cardiac defibrillation electrodes into a patient, said tool comprising:

an elongate electrode support tube having a rounded distal end and a proximal end, said electrode support tube exhibiting a diameter;

a finger grip connected to said electrode support tube toward said proximal end thereof;

an actuating rod slidably disposed coextensively within said electrode support tube, said actuating rod having a distal end extending beyond the rounded distal end of said electrode support tube and a proximal end extending beyond said proximal end of said electrode support tube;

a blunt conically shaped distal tip connected to said distal end of said actuating rod, said distal tip having a portion with a diameter larger than the diameter of said electrode support tube, said distal tip further having an inner surface for engaging said rounded distal end of said electrode support tube;

a palm member connected to said proximal end of said actuating rod; and resilient means for exerting a force on said actuating rod tending to withdraw said actuating rod out through said proximal end of said electrode support tube, such withdrawal being prevented by engagement of said inner surface of said distal tip with said rounded distal end of said electrode support tube.

2. The tool of claim 1, wherein said distal tip has a base, said base having a beveled edge.

3. The tool of claim 2, further comprising a longitudinally slidable sleeve circumferentially surrounding said electrode support tube, said slidable sleeve being slidable between a first position toward said distal end of said electrode support tube and second position toward said proximal end of said electrode support tube.

4. The tool of claim 1, wherein said finger grip comprises a central body portion which receives said proximal end of said electrode support tube, and a pair of diametrically opposed finger hooks extending radially outward from said central body portion.

5. The tool of claim 1, wherein said resilient means comprises a coil spring circumferentially surrounding said actuating rod between said finger grip and said palm member, said coil spring being in a compressed state so as to exert a force tending to separate said finger grip from said palm member and thereby tending to withdraw said actuating rod out through said proximal end of said electrode support tube, said coil spring being further compressible so as to allow translation of said actuating rod with respect to said electrode support tube such that said inner surface of said distal tip disengages said rounded distal end of said electrode support tube.

6. The tool of claim 1, wherein said distal tip has a base and said base comprises a generally concave shape thereby defining an annular void between said distal tip and said rounded distal end of said electrode support tube.

7. The tool of claim 1, wherein said electrode support tube and said actuating rod have a circular cross section.

8. The tool of claim 1, wherein said electrode support tube and said actuating rod have an elliptical cross section.

9. A method for inserting a cardiac defibrillation electrode into the body of a patient, said method comprising the steps of:

creating a puncture wound in the chest wall of the patient;

squeezing a finger grip of an applicator tool toward a palm member of the applicator tool, thereby causing a distal tip of the applicator tool to disengage a rounded distal end of an electrode support tube of the applicator tool;

wrapping said cardiac defibrillation electrode circumferentially around said electrode support tube such that a distal end of the cardiac defibrillation electrode is received in a space which separates the rounded distal end of the electrode support tube from the distal tip;

immobilizing the cardiac defibrillation electrode on the applicator tool by releasing the finger grip and palm member thereby allowing the rounded distal end of the electrode support tube and the distal tip to engage the distal end of the cardiac defibrillation electrode;

advancing the distal tip of the applicator tool through the puncture wound toward a desired position where the cardiac defibrillation electrode is to be deployed;

subsequently squeezing the finger grip toward the palm member to release the electrode from the applicator tool; and withdrawing said applicator tool from the patient.

10. The method of claim 9, further comprising the step of sliding a sleeve which circumferentially surrounds the electrode support tube into abutment with the distal tip after said step of subsequently squeezing, such that snagging of tissue is prevented during said step of withdrawing.

11. The method of claim 9, further comprising the step of suturing said cardiac defibrillation electrode in said desired position after said step of withdrawing.

12. The method of claim 9, further comprising the step of stapling said cardiac defibrillation electrode in said desired position after said step of withdrawing.

* * * * *